United States Patent [19]
Rooney et al.

[11] Patent Number: 5,518,503
[45] Date of Patent: May 21, 1996

[54] ORAL EXAMINATION TONGUE DEPRESSOR

[76] Inventors: Christopher F. Rooney, 8300 SW. 8th, Oklahoma City, Okla. 73128; William J. Hale, 35 SE. 33rd, Edmond, Okla. 73013

[21] Appl. No.: 419,496

[22] Filed: Apr. 10, 1995

Related U.S. Application Data

[63] Continuation-in-part of Ser. No. 18,557, Feb. 9, 1994, Pat. No. Des. 359,556.
[51] Int. Cl.⁶ .............................. A61B 13/00; A61C 17/10
[52] U.S. Cl. ................................................ 600/240
[58] Field of Search ...................... D24/136; 128/3, 128/10, 15, 16, 20; 606/1, 119, 161, 162, 190; 600/240

[56] References Cited

U.S. PATENT DOCUMENTS

| | | | |
|---|---|---|---|
| D. 344,335 | 2/1994 | Elisha | D24/136 |
| 1,396,933 | 11/1921 | Jacoby | 128/15 |
| 1,613,373 | 1/1927 | Beck | 128/15 |
| 2,723,661 | 11/1955 | Hull | D24/136 |

FOREIGN PATENT DOCUMENTS

| | | | |
|---|---|---|---|
| 0490840 | 7/1992 | European Pat. Off. | 128/15 |
| 2302614 | 7/1974 | Germany | 128/15 |

*Primary Examiner*—Stephen C. Pellegrino
*Assistant Examiner*—Glenn Dawson
*Attorney, Agent, or Firm*—Robert K. Rhea

[57] ABSTRACT

An elongated relatively thin longitudinally arcuately bowed disposable tongue depressor having the major portion of its length characterized by a transverse wide substantially V-shape and having a flesh adhesive texture on the respective end portions of its ventral surface.

2 Claims, 1 Drawing Sheet

ORAL EXAMINATION TONGUE DEPRESSOR

CROSS REFERENCE TO RELATED APPLICATION

This application is a continuation-in-part of a design application filed by us on Feb. 9, 1994 under Ser. No. 29/018,557 for Oral Examination Tongue Depressor, now U.S. Pat. No. Des. 359,556.

BACKGROUND OF THE INVENTION

1. Field of the Invention

This invention relates to medical equipment and more particularly to an improvement in a tongue depressor.

2. Description of the Prior Art

Conventional tongue depressors comprise an elongated relatively thin length of material (usually wood) having parallel side edges and part circular end surfaces. The present invention is an improvement over conventional tongue depressors by forming an elongated longitudinally arcuately curved structurally reinforced member which conforms to the user's hand and the arched tongue of a patient.

We do not know of any patents disclosing the features of our improved tongue depressor.

SUMMARY OF THE INVENTION

As an article of manufacture the tongue depressor is preferably formed from plastic material. The tongue depressor is elongated, relatively narrow and thin when compared with its longitudinal and transverse dimensions and is longitudinally arcuately bowed on a selected radius, having part circular end surfaces and opposing side surfaces converging toward one end.

The convex surface of the depressor forms its top surface and its opposite concave surface forms the ventral or bottom surface when in use. At its respective end portions, the bottom surface is provided with a friction inducing texture when applied to a patient's tongue and that area between the friction inducing areas describes a wide V-shape in cross section.

The principle objects of the invention are: to provide a longitudinally arcuately curved tongue depressor having a friction inducing texture on its ventral surface at respective end portions to provide adhesive action in response to applied pressure; follows the curve of the oral cavity conforming to and griping a patient's tongue to keep it from buckling; allows maximum pressure to be applied with minimal deflection and without danger to a patient; provides a total view of the oro pharynx and the throat area but does not touch the back of the throat; and, with less time required and minimal discomfort to the patient.

DESCRIPTION OF THE PREFERRED EMBODIMENTS

Figure 1:
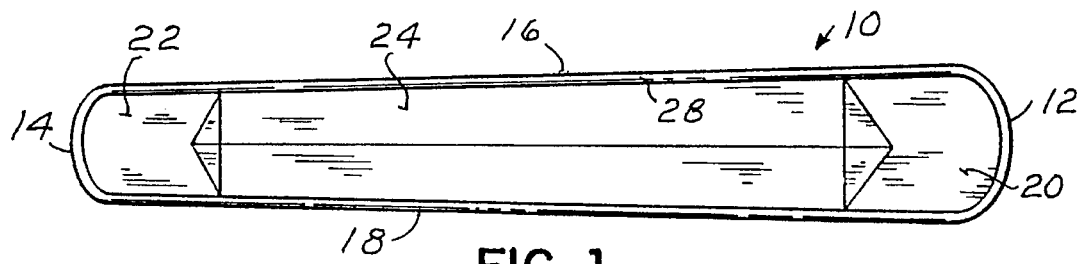
FIG. 1 is a top view of the tongue depressor.

Like characters of reference designate like parts in those figures of the drawings in which they occur.

Referring first to FIGS. 1–5, the reference numeral 10 indicates an elongated tongue depressor longitudinally bowed on a selected radius for example, 8¾ inches (21.6 cm) (FIG. 3) which enhances visibility of the mouth and throat area by lowering the position of a physician's hand relative to a patients mouth and at least partially conforming to the arch of an extended tongue.

Figure 2:
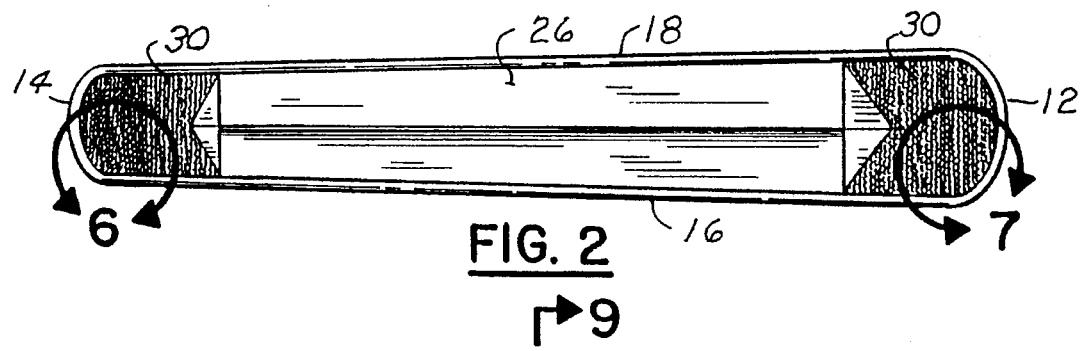
FIG. 2 is bottom view.
Figure 3:
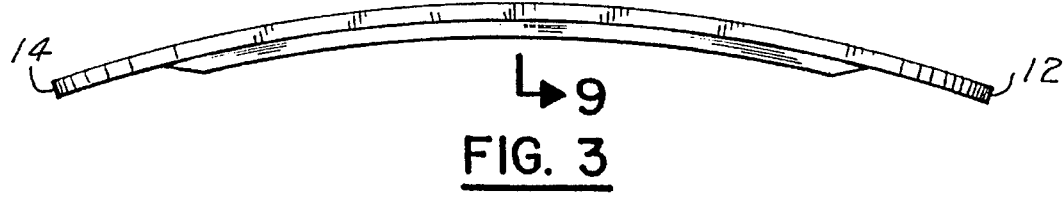
FIG. 3 is side elevational view.
Figure 4:
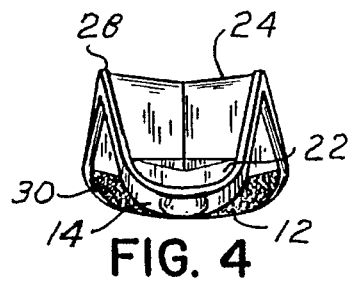
FIGS. 4 and 5 are left and right end elevational views, respectively.
Figure 5:
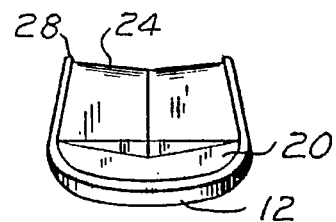

Each of its end surfaces 12 and 14 are formed part circular and merge with the respective side surface 16 and 18 (FIGS. 1 and 2). The width of its larger end portion 20 adjacent the end surface 12 is approximately one inch (2.54 cm) and the width of its smaller end portion 22 adjacent the end surface 14 is approximately three-fourths inch (1.9 cm) thus, forming a tongue depressor in which the side edges converge toward its end 14, for use with children.

The thickness of the tongue depressor relative to its length and width is relatively thin, for example, three millimeters. The convex surface of the tongue depressor forms its top surface 24 while its concave surface forms its bottom or ventral surface 26.

Figure 9:
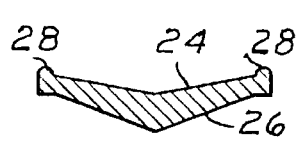

Between its substantially planar end portions 20 and 22 and side surfaces 16 and 18, the tongue depressor converges downwardly to form a wide V-shape, as viewed in FIG. 9, to add rigidity to the tongue depressor and form a saliva conducting V-shape on its upper or top surface 24.

An upstanding transversely arcuate rib or protrusion 28 on the convex surface 24 of the tongue depressor adjacent the respective side and end surface increases the depth of the V-shape and presents a smooth surface where the tongue depressor may contact areas of the mouth, throat, or tongue.

Figure 6:
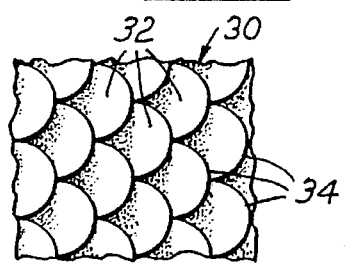
FIGS. 6 and 7 are fragmentary elevational views, to an enlarged scale, of the areas substantially surrounded by the arrows 6 and 7 of FIG. 2.
Figure 8:
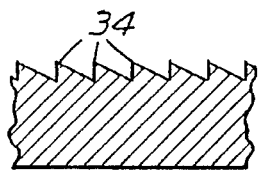
FIG. 8 is vertical cross sectional view, to a further enlarged scale, taken substantially along the line 8—8 of FIG. 7; and, FIG. 9 is a vertical cross sectional view taken substantially along the line 9—9 of FIG. 3.
Figure 7:
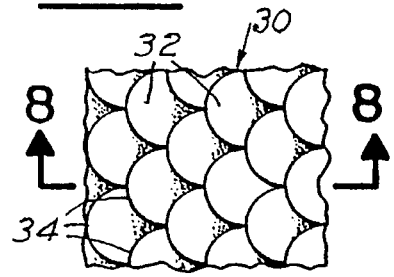

The top surface of the respective end portion 20 and 22, inwardly of its rib 28 are provided with an abrasive texture 30 which is fish scale-like in general appearance, being formed by semicircular overlapping members, in top view (FIGS. 6 and 7). The semicircular areas are disposed toward the medial portion of the depressor and are top surface etched away, so that the central portion of the semicircular members form a series of serrations or teeth 34 (FIG. 8) facing toward the depressor central portion, acting in unison to grip the surface of the tongue in an adhesive fashion for resisting lateral and longitudinal movement of the depressor relative to the tongue when pressure is mannually applied to the dorsal end of the tongue depressor, when contacting a patient's tongue, in a downward and forward motion by a physician. This results in depressing the rearward end portion of the tongue adjacent the oro phalanx and provides a full view of the throat area.

Obviously the invention is susceptible to changes or alterations without defeating its practicability. Therefore, we do not wish to be confined to the preferred embodiment shown in the drawings and described herein.

We claim:

1. A tongue depressor, comprising;

an elongated member arcuately bowed longitudinally, relatively narrow and thin when compared with its length, formed from rigid material having a transverse wide V-shape between its end portions and having parallel top and ventral surfaces at respective end portions terminating in part circular end surfaces and having opposite side surfaces converging toward one end portion;

an endless upstanding rib on said top surface adjacent the opposite side surfaces and part circular end surfaces; and, a friction inducing fish scale-like texture on the ventral surface of each said end portion for resisting lateral and outward longitudinal movement of the depressor relative to a patient's tongue in response to pressure manually applied to the depressor when in use.

2. A tongue depressor, comprising;

an elongated member arcuately bowed longitudinally, relatively narrow and thin when compared with its length, formed from rigid material having opposite side surfaces and having a transverse wide V-shape between its end portions and having parallel top and ventral surfaces at respective end portions terminating in part circular end surfaces;

an endless upstanding rib on said top surface adjacent the opposite side surfaces and part circular end surfaces; and, a friction inducing fish scale-like texture on the ventral surface of one end portion for resisting longitudinal movement of the depressor in an outward direction relative to a patient's tongue in response to pressure manually applied to the depressor when in use.

* * * * *